United States Patent [19]
Drent

[11] Patent Number: 4,739,109
[45] Date of Patent: Apr. 19, 1988

[54] PROCESS FOR THE CARBONYLATION OF ACETYLENICALLY UNSATURATED COMPOUNDS

[75] Inventor: Eit Drent, CM Amsterdam, Netherlands

[73] Assignee: Shell Oil Company, Houston, Tex.

[21] Appl. No.: 802,804

[22] Filed: Nov. 27, 1985

[30] Foreign Application Priority Data

Dec. 21, 1984 [GB] United Kingdom ............... 8432376

[51] Int. Cl.$^4$ ...................... C07C 51/14; C07C 67/38
[52] U.S. Cl. .................................... 560/207; 560/104; 560/114; 560/130; 562/406; 562/497; 562/522
[58] Field of Search ............... 560/207, 104, 114, 130; 562/522, 497, 406; 260/546

[56] References Cited

U.S. PATENT DOCUMENTS

| | | | |
|---|---|---|---|
| 2,738,364 | 3/1966 | Reppe et al. | 562/522 |
| 3,641,137 | 2/1972 | Fenton | 562/522 |
| 3,709,927 | 1/1973 | Kunichika | 562/522 |
| 3,952,034 | 4/1976 | Thompson | 560/207 |
| 4,055,721 | 10/1977 | Kawata et al. | 560/207 |

OTHER PUBLICATIONS

Chemical Abstracts 88 (1978), p. 456, 37267k.
Chemical Abstracts 94 (1981), p. 683, 138866j.

Primary Examiner—Michael L. Shippen

[57] ABSTRACT

Process for the carbonylation of an acetylenically unsaturated compound with CO in the presence of an alcohol and/or water and of a catalyst formed by combining a Pd(II) compound, an organic phosphine and a protonic acid, with the exception of hydrohalogenic acids.

27 Claims, No Drawings

PROCESS FOR THE CARBONYLATION OF ACETYLENICALLY UNSATURATED COMPOUNDS

FIELD OF THE INVENTION

The invention relates to a process for the carbonylation of an acetylenically unsaturated compound with carbon monoxide in the presence of an alcohol and/or water in a liquid phase.

BACKGROUND OF THE INVENTION

It is known that acetylenically unsaturated compounds may be carbonylated in the presence of an alcohol or water to yield alpha-beta-olefinically unsaturated esters or acids, respectively. However, the known processes have low selectivities to such esters or acids, which render them rather unattractive for use on a technical scale.

It has now been found that in the carbonylation of acetylenically unsaturated compounds the selectivity to alpha-beta-olefinically unsaturated esters or acids is strongly increased and in many cases the reaction rate much enhanced by carrying out the reaction in the presence of a special catalytic system.

SUMMARY OF THE INVENTION

The invention relates to a process for the carbonylation of an acetylenically unsaturated compound with carbon monoxide in the presence of an alcohol and/or water in a liquid phase, which process is carried out in the presence of a catalytic system formed by combining:
(a) a compound of divalent palladium,
(b) an organic phosphine, and
(c) a protonic acid, with the exception of hydrohalogenic acids.

DESCRIPTION OF THE PREFERRED EMBODIMENTS

The selectivity to alpha-beta-olefinically unsaturated compounds expressed in a percentage is defined as $(a/b) \times 100$ in which "a" is the amount of acetylenically unsaturated compound that has been converted into alpha-beta-olefinically unsaturated compound and "b" is the total amount of acetylenically unsaturated compound that has been converted.

The organic phosphine may be primary, secondary or, which is preferred, tertiary. Suitable phosphines include those of the general formula I

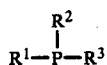

in which $R^1$ represents an optionally substituted aryl group and $R^2$ and $R^3$ each an optionally substituted alkyl, optionally substituted cycloalkyl or optionally substituted aryl group, or $R^2$ and $R^3$ together represent an optionally substituted alkylene or phosphacycloalkylene group. Preferably, any alkyl group has up to 20 carbon atoms, any cycloalkyl group up to 5 to 7 carbon atoms in the ring and any aryl group up to 18 carbon atoms in the ring. Any aryl group may be an anthryl, naphthyl or, which is preferred, a phenyl group. Phosphines of the general formula I in which $R^1$ and $R^2$ each represent an optionally substituted phenyl group are a preferred group of phosphines; within this group those phosphines in which $R^3$ also represents an optionally substituted phenyl group are particularly preferred.

An optionally substituted alkylene group formed by $R^2$ and $R^3$ suitably has in the range of from 4 to 9 and particularly from 6 to 8 carbon atoms, and such a group may form a monocyclic or bicyclic ring containing the phosphorus atom. An example of such a compound is

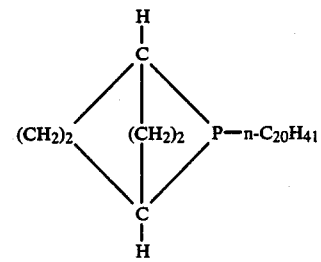

Another preferred group of organic phosphines are those of the general formula I in which $R^3$ represents a chain of carbon atoms ending with the group $-PR^4R^5$, in which $R^4$ represents an optionally substituted phenyl group and $R^5$ an optionally substituted alkyl, optionally substituted cycloalkyl or optionally substituted phenyl group. Preferably, $R^4$ and $R^5$ are equal to $R^1$ and $R^2$, respectively. The chain of carbon atoms suitably comprises 2 to 6 carbon atoms.

According to a preferred embodiment of the present invention in which not only very high selectivities to alpha-beta-olefinically unsaturated esters or acids but also very high reaction rates are obtained, the organic phosphine is a phosphine of the general formual I in which any aryl group is unsubstituted or carries an electron-donating substituent and the protonic acid is a non-carboxylic protonic acid having a $pK_a$ greater than 0.1 (measured at 18° C. in aqueous solution) or a carboxylic acid. Very good results have been obtained with triphenylphosphine. Examples of the electron-donating substituents are p-alkoxy groups, particularly those having not more than 5 carbon atoms in the alkoxy group, for example p-methoxy and p-ethoxy groups. Very good results have been obtained with tri(p-methoxyphenyl)phosphine. Other examples of suitable electron-donating groups are methyl, ethyl, n-propyl, isopropyl, tert-butyl, dimethylamino or diethylamino groups.

Other examples of suitable phosphines are phenyldiethylphosphine, ethyldiphenylphosphine, phenyldipropylphosphine and propyldiphenylphosphine. Further examples of suitable phosphines are 1,2-ethanediylbisdiphenylphosphine, 1,2-ethenediylbisdiphenylphosphine, 1,2-ethynediylbisdiphenylphosphine, 1,2-ethanediylbisdi(trifluoromethyl)-phosphine, 1,2-phenylenebisdiphenylphosphine, 1,2-tetrafluorocyclobutenediylbisdiphenylphosphine, 1,2-hexafluorocyclopentenediylbisdiphenylphosphine, 1,2-octafluorocyclohexenediylbisdiphenylphosphine, 1,4-diphenyl1,4-diphosphacyclohexane, bis(o-diphenylphosphinophenyl)phenylphosphine and tris(o-diphenylphosphinophenyl)phosphine. Very good results have been obtained with 1,5-di(diphenylphosphino)pentane. Mixtures of organic phosphines be used.

Preferred non-carboxylic acids having a $pK_a$ greater than 1.0 are orthophosphoric acid, benzenephosphonic acid and pyrophosphoric acid. Another example of such acids is arsenic acid. Examples of suitable carboxylic acids are formic acid, acetic acid, acetoacetic acid, benzoic acid, n-butyric acid, monochloroacetic acid, dichloroacetic acid, oxalic acid and terephthalic acid. The carboxylic acid preferably has $pK_a$ not greater than 1.0 (measured at 18° C. in aqueous solution). Very good results have been obtained with trifluoroacetic acid. Another example of a suitable carboxylic acid is trichloroacetic acid. Mixtures of non-carboxylic protonic acids having a $pK_a$ greater than 1.0 and carboxylic acids may be used.

Very high selectivities to alpha-beta-olefinically unsaturated esters or acids at still acceptable rates have been observed when the organic phosphine is one of the general formula I in which any aryl group is unsubstituted or carries an electron-donating substituent and the protonic acid is a non-carboxylic protonic acid having a $pK_a$ not greater than 1.0 (measured in 18° C. in aqueous solution). Examples of such acids are p-toluenesolphonic acid, benzenesulphonic acid and naphthalenesulphonic acid.

According to another preferred embodiment of the present invention in which not only very high selectivities to alpha-beta-olefinically unsaturated esters or acids but also very high reaction rates are obtained, the organic phosphine is a phosphine of the general formula I in which $R^1$, $R^2$ and $R^3$ each represent a phenyl group carrying an electron-withdrawing substituent and the protonic acid is a non-carboxylic protonic acid having a $pK_a$ not greater than 1.0 (measured at 18° C. in aqueous solution). Examples of electron-withdrawing substituents are chlorine, bromine, monochloromethyl, trichloromethyl, trifluoromethyl, nitro and m-methoxy groups. Very good results have been obtained with trihalomethyl groups, in particular with trifluoromethyl groups. Preferred phosphines are tri(p-chlorophenyl)phosphine and tri(m-trifluoromethylphenyl)phosphine.

The non-carboxylic protonic acid having $pK_a$ not greater than 1.0 preferably has a non-coordinating anion, by which is meant that little or no-covalent interaction takes place between the palladium and the anion (cf. British patent application No. 2,058,074). Typical examples of such anions are $PF_6^-$, $SbF_6^-$, $BF_4^-$ and $ClO_4^-$. Preferred acids are sulphonic acids and acids that can be formed, possibly in situ, by interacting a Lewis acid such as, for example, $BF_3$, $AsF_5$, $SbF_5$, $PF_5$ $TaF_5$ or $NbF_5$ with a Broensted acid such as, for example, a hydrogen halide, in particular HF, or fluorosulphonic acid, orthophosphoric acid or sulphuric acid. Specific examples of acids of the latter type are fluorosilicic acid $HPF_6$ and $HPF_6$. Examples of usable sulphonic acids are fluorosulphonic acid and chlorosulphonic acid and the hereinafter specified sulphonic acids.

A preferred group of non-carboxylic protonic acids having a $pK_a$ not greater than 1.0 are those having the general formula II

$$R-\underset{\underset{O}{\|}}{\overset{\overset{O}{\|}}{Z}}-O-H \qquad (II)$$

wherein Z represents sulphur or chlorine and, if Z is chlorine, R represents oxygen and, if Z is sulphur, R represents an OH group or an optionally substituted hydrocarbon group.

When the hereinbefore-stated acids of the general formula II are used in the process according to the invention, the anions thereof can be considered to be non-coordinating.

The optionally substituted hydrocarbon group represented by R is preferably an alkyl, aryl, aralkyl or alkaryl group having 1 to 30, in particular 1 to 14, carbon atoms. The hydrocarbon group may, for example, be substituted with halogen atoms, in particular fluorine atoms. Examples of suitable acids of the general formula II are perchloric acid, sulphuric acid, 2-hydroxypropane-2-sulphonic acid, benzenesulphonic acid, 1-naphthalenesulphonic acid, 2-naphthalenesulphonic acid, p-toluenesulphonic acid and trifluoromethanesulphonic acid, p-toluenesulphonic acid being the most preferred.

Very high selectivities to alpha-beta-olefinically unsaturated esters or acids at still acceptable reaction rates have been observed when the organic phosphine is an organic phosphine of the general formula I in which any aryl group carries an electron-withdrawing substituent and the protonic acid is a carboxylic acid having a $pK_a$ not greater than 1.0 or a non-carboxylic protonic acid having a $pK_a$ greater than 1.0 Examples of acids of the former and of the latter type have been given hereinbefore.

Both homogeneous and heterogeneous palladium catalysts may be used in the process according to the invention. Homogeneous catalysts are preferred. Suitable homogeneous catalysts are the salts of palladium with, for example, nitric acid, sulphuric acid or alkanoic acids having not more than 12 carbon atoms per molecule. Salts of hydrohalogenic acids may, in principle, be used as well, but they have the drawback that the halogen ion may have a corrosive effect. A catalyst used by preference is palladium acetate. Moreover, palladium complexes may be used, for instance palladium acetylacetonate, tetrakistriphenylphosphinepalladium, bis-tri-o-tolylphosphinepalladium acetate or bistriphenylphosphinepalladium sulphate. Palladium bonded to an ion exchanger—for instance an inon exchanger comprising sulphonic acid groups—is an example of a suitable heterogeneous catalyst.

The quantity of the compound of divalent palladium is not critical. Preference is given to the use of quantities in the range between $10^{-5}$ and $10^{-1}$ gram atom palladium per mol of acetylenically unsaturated compound.

The molar ratio of organic phosphine to palladium is not critical and may vary between wide limits. If less than 5 mol of the organic phosphine are used per gram atom of palladium, selectivity to alpha-beta-olefinically unsaturated ester or acid is still very high, but the reaction rate is moderate. Very high selectivities and very high reaction rates are obtained when more than 5 and in particular more than 20 mol of the organic phosphine are used per gram atom of palladium. In general, more than 500 mol of the organic phosphine per gram atom of palladium need not be used.

The number of equivalents of the organic phosphine which is used per equivalent of protonic acid is not critical and may vary between wide limits. Suitably, in the range of from 0.5 to 50 equivalents of the organic phosphine are used per equivalent of the protonic acid.

A separate solvent is not essential in the process according to the invention, and often a large excess of one of the reactants, usually the alcohol, may form a convenient liquid phase. However, it may in some cases be desirable to use a separate solvent and any inert solvent may be used. A suitable solvent may for example be selected from sulphoxides and sulphones, for example dimethyl sulphoxide, diisopropyl sulphone or tetrahydrothiophene 1,1-dioxide (also referred to as "sulfolane"), ketones, for example acetone or methyl isobutyl ketone, and ethers. Very good results have been obtained with ethers, in particular with anisole, 2,5,8-trioxanonane (also referred to as "diglyme") and diphenyl ether. Another example of a suitable ether is diisopropyl ether.

The process according to the invention permits the use of very mild reaction conditions. Temperatures in the range of from about 50° C. to about 200° C. especially about 100° C. to about 150° C., are generally suitable. The pressure may vary over a wide range. Generally, a pressure in the range of from 1 to about 100 bar is suitable, with pressures of from about 5 to 50 bar being preferred. Pressures higher than 100 bar may be used, but are usually economically unattractive.

The molar ratio of alcohol (or water) to acetylenically unsaturated bonds is not critical, may vary between wide limits and is generally in the range of from 0.1:1 to 10:1.

The process according to the invention may be carried out using a wide variety of acetylenically unsaturated compounds and it is not excluded that such compounds carry one or more substituents which are inert under the reaction conditions, such as halogen atoms and cyano, ester, alkoxy and aryl groups. In addition, the acetylenically unsaturated compound may contain one or more substituents which are not inert under the reaction conditions, for example hydroxy groups. The fate of such groups will depend on the precise reaction conditions. One or more acetylenically unsaturated bonds may be present in any position in the carbon chain. Very good results have been obtained with unsubstituted alkynes, particularly with those having up to 20 carbon atoms per molecule, more particularly with ethyne and propyne. Other examples of suitable alkynes are 1-butyne, 2-butyne, 1-pentyne, 1-hexyne, 1-heptyne, 1-octyne, 2-octyne, 4-octyne, 5-methyl-3-heptyne, 4-propyl-2-pentyne, 1-nonyne, benzylethyne and cyclohexylethyne.

A wide range of alcohols may be used as reactant in the process of the invention. For example, the alcohol may be aliphatic, cycloaliphatic or aromatic, and may carry one or more inert substituents, for example halogen atoms and cyano, ester, alkoxy and aryl groups. The alcohol suitably contains up to 20 carbon atoms per molecule. One or more hydroxy groups may be present, in which case different products can be obtained as desired depending upon the molar ration of reactants used. For example, a trihydric alcohol can be reacted with a small quantity of acetylenically unsaturated compound to produce a mono-ester, or with a large quantity of acetylenically unsaturated compound to produce a tri-ester.

Thus the choice of alcohol depends solely on the desired product. The use of water produces alpha-beta unsaturated carboxylic acids as the initial product. The use of alcohols produces alpha-beta-unsaturated esters, and these can of course be poly-esters as described above. Alkanols such as methanol, ethanol, propanol or 2,2-dihydroxymethyl-1-butanol, and alcohols containing ether linkages, for example triethylene glycol, all produce useful products.

The following Examples further illustrate the invention and are not to be construed as limiting the invention.

EXAMPLES 1-18

A 250-ml magnetically stirred Hastelloy C autoclave ("Hastelloy" is a trademark) was charged with 10 ml methanol, 40 ml of a solvent and with palladium acetate, a phosphine and a protonic acid. Table 1 hereinafter states which solvent, phosphine and protonic acid was used and the quantities of each of the three catalyst components. The autoclave was flushed with carbon monoxide, filled with propyne and carbon monoxide at the pressures stated in Table 1, sealed and heated to the temperature stated in Table 1. After the reaction the contents of the autoclave were analyzed by menas of gas-liquid chromatography. The reaction rates and the selectivities to methyl methacrylate are presented in Table 1.

The table shows that the highest reaction rates have been observed when using orthophosphoric acid.

Comparison of Examples 2 and 3 shows that increasing the temperature by 10° C. considerably increases the reaction rate whilst the very high selectivity is maintained.

Comparison of Examples 2 and 4 shows that it is preferred to apply more than 5 mol of phosphine per gram atom of palladium, the reaction rate in Example 2 being 11 times higher than in Example 4.

Comparison of Examples 5 and 9 shows that with triphenylphosphine higher reaction rates and higher selectivities are obtained than with tricyclohexylphosphine. The reaction rate in Example 9 was 100 mol propyne per gram atom palladium per hour for 30 min and sharply decreased after this period.

Examples 11-14 show that with use of p-toluenesulphonic acid, being a strong protonic acid, selectivity is still high but that the reaction rate is lower than in Examples 1-10, 15 and 17 where protonic acids having a $pK_a$ higher than 1.0 have been used.

Example 16 shows that very high reaction rates and selectivities to methyl methacrylated are found with trifluoroacetic acid.

EXAMPLE 19

The experiment of Example 5 was repeated using 10 ml liquid propene in addition to propyne and a temperature of 110° C. instead of 115° C. A reaction rate of 230 mol of propyne per gram atom of palladium per hour and a selectivity to methyl methacrylate of 95% were observed. Methyl isobutyrate could not be detected in the reaction mixture, indicating that no propene had reacted.

TABLE 1

| Example No. | Palladium acetate, mmol | Phosphine | Amount, mmol | Protonic acid | Amount, mmol | Solvent | Partial pressure carbon monoxide, bar | Partial pressure propyne, bar | Temp., °C. | Reaction rate, mol propyne per gram atom Pd per hour | Selectivity, %, to methyl methacrylate |
|---|---|---|---|---|---|---|---|---|---|---|---|
| 1 | 0.5 | Triphenyl- | 10 | Orthophos- | 10 | Anisole | 20 | 2 | 115 | more than | 92 |

TABLE 1-continued

| Example No. | Palladium acetate, mmol | Phosphine | Amount, mmol | Protonic acid | Amount, mmol | Solvent | Partial pressure carbon monoxide, bar | Partial pressure propyne, bar | Temp., °C. | Reaction rate, mol propyne per gram atom Pd per hour | Selectivity, %, to methyl methacrylate |
|---|---|---|---|---|---|---|---|---|---|---|---|
| 2 | 0.2 | phosphine Triphenyl-phosphine | 20 | phoric acid benzene-phosphonic acid | 10 | " | 20 | 2 | 115 | 500 220 | 95 |
| 3 | 0.2 | Triphenyl-phosphine | 20 | benzene-phosphonic acid | 10 | " | 20 | 2 | 125 | 330 | 95 |
| 4 | 0.2 | Triphenyl-phosphine | 1 | benzene-phosphonic acid | 10 | " | 20 | 2 | 115 | 20 | 96 |
| 5 | 0.2 | Triphenyl-phosphine | 10 | benzene-phosphonic acid | 10 | diphenyl ether | 20 | 2 | 115 | 450 | 94 |
| 6 | 0.2 | tri(p-methoxyphenyl)phosphine | 10 | benzene-phosphonic acid | 10 | anisole | 20 | 2 | 115 | 300 | 95 |
| 7 | 0.2 | 1,5-di(diphenylphosphino)pentane | 5 | benzene-phosphonic acid | 1 | " | 20 | 2 | 115 | 350 | 95 |
| 8 | 0.2 | phenyldiethylphosphine | 10 | benzene-phosphonic acid | 10 | " | 20 | 2 | 115 | 160 | 94 |
| 9 | 0.2 | tricyclohexylphosphine | 10 | benzene-phosphonic acid | 10 | " | 20 | 2 | 115 | 100 | 75 |
| 10 | 0.2 | triphenyl-phosphine | 10 | benzene-phosphonic acid p-toluene-sulphonic acid | 5 5 | " | 20 | 2 | 115 | 450 | 93 |
| 11 | 0.5 | triphenyl-phosphine | 20 | p-toluene-sulphonic acid | 5 | diglyme | 18 | 2 | 125 | 15 | 92 |
| 12 | 0.5 | triphenyl-phosphine | 5 | p-toluene-sulphonic acid | 3 | " | 20 | 2 | 115 | 10 | 90 |
| 13 | 0.5 | triphenyl-phosphine 1,3-di(diphenylphosphino)propane | 20 0.5 | p-toluene-sulphonic acid | 5 | anisole | 16 | 4 | 115 | 25 | 85 |
| 14 | 0.5 | triphenyl-phosphine 1,3-di(diphenylphosphino)propane | 20 0.5 | p-toluene-sulphonic acid | 10 | " | 18 | 4 | 115 | 40 | 88 |
| 15 | 0.2 | triphenyl-phosphine | 10 | pyrophosphoric acid | 5 | " | 20 | 2 | 115 | 250 | 95 |
| 16 | 0.2 | triphenyl-phosphine | 10 | trifluoroacetic acid | 10 | diphenyl ether | 20 | 2 | 115 | 300 | 94 |
| 17 | 0.2 | triphenyl-phosphine | 10 | methacrylic acid | 10 | anisole | 20 | 2 | 115 | 130 | 70 |
| 18 | 0.2 | triphenyl-phosphine | 1 | methacrylic acid | 10 | " | 20 | 2 | 115 | 60 | 49 |

EXAMPLE 20

The experiment of Example 5 was repeated using 10 g of phenol instead of 10 ml of methanol and 40 ml of anisole instead of 40 ml of diphenyl ether. A reaction rate of 210 mol of propyne per gram atom of palladium per hour and a selectivity to phenyl methacrylate of 97% were observed.

EXAMPLE 21

The experiment of Example 5 was repeated using 100 mmol of diacetone d-glucose instead of 10 ml of methanol, 50 ml of toluene instead of 40 ml of diphenyl ether and a temperature of 100° C. instead 115° C. A reaction rate of 100 mol of propyne per gram atom of palladium per hour and a selectivity of more than 95% to the corresponding methacrylic ester were observed.

EXAMPLE 22

The experiment of Example 5 was repeated using 10 ml of water instead of 10 ml of methanol and 40 ml of diglyme instead of 40 ml of diphenyl ether. After a reaction time of 2 hours a reaction rate of 150 mol of propyne per gram atom of palladium per hour and a selectivity to methacrylic acid of 95% were observed.

Comparative Experiment A

The experiment of Example 5 was repeated in the absence of a protonic acid and using 40 ml of anisole instead of 40 ml of diphenyl ether. After a reaction time of 5 hours a reaction rate of less than 1 mol of propyne per gram atom of palladium per hour was observed.

Comparative Experiment B

The experiment of Example 1 was repeated using 5 mmol instead of 10 mmol of triphenylphosphine, 3 mmol of hydrogen chloride instead of 10 mmol of orthophosphoric acid and 40 ml of diglyme instead of 40 ml of anisole. A reaction rate of 60 mol of propyne per gram atom of palladium per hour and a selectivity to methyl methacrylate of 56% were observed.

EXAMPLES 23-27

EXAMPLE 28

An autoclave as used in Example 1 was charged with palladium acetate (0.2 mmol), tri(m-chlorophenyl)phosphine (10 mmol), p-toluenesulphonic acid (10 mmol), 40 ml diglyme and water (10 ml). The autoclave was flushed with carbon monoxide, filled with propyne at a pressure of 2 bar and carbon monoxide at a pressure of 20 bar, sealed and heated to a temperature of 115° C. for a period of 5 hours. The reaction rate was 300 mol propyne per gram atom palladium per hour. The selectivity to methacrylic acid was 95%.

EXAMPLE 29

This Example only differs from Example 24 in that the propyne was replaced with ethyne of a pressure of 1 bar. After a reaction time of 0.5 h the reaction rate was more than 100 mol ethyne per gram atom palladium per hour and the selectivity to methyl acrylate was more than 95%.

TABLE 2

| Example No. | Palladium acetate, mmol | Phosphine | Amount, mmol | Protonic acid | Amount, mmol | Reaction time, h | Reaction rate, mol propyne per gram atom Pd per h | Selectivity %, to methyl methacrylate |
|---|---|---|---|---|---|---|---|---|
| 23 | 0.5 | Tri(p-chlorophenyl)phosphine | 10 | p-toluenesulphonic acid | 5 | 2 | 100 | 82 |
| 24 | 0.5 | Tri(p-chlorophenyl)phosphine | 20 | p-toluenesulphonic acid | 5 | 2 | 160 | 89 |
| 25 | 0.5 | tri(m-trifluoromethylphenyl)phosphine | 10 | p-toluenesulphonic acid | 10 | 1 | more than 500 | 85 |
| 26 | 0.2 | tri(m-chlorophenyl)phosphine | 10 | trifluoroacetic acid | 10 | 5 | 10 | 95 |
| 27 | 0.2 | tri(m-chlorophenyl)phosphine | 10 | pyrophosphoric acid | 5 | 5 | 20 | 94 |

A 250-ml magnetically stirred Hastelloy C autoclave ("Hastelloy" is a trademark) was charged with 40 ml anisole, 10 ml methanol and palladium acetate, a phosphine having an electron-withdrawing substituent and a protonic acid. Table 2 hereinafter states which phosphine and protonic acid was used and mentions the quantities of the three catalyst components. The autoclave was flushed with carbon monoxide, filled with propyne at a partial pressure of 2 bar and with carbon monoxide at a partial pressure of 20 bar, sealed and heated to a temperature of 115° C. After the reaction time stated in Table 2 the contents of the autoclave were analyzed by means of gas-liquid chromatography. The reaction rates and selectivities to methyl methacrylate are presented in Table 2. Examples 23-25 show that very high reaction rates and selectivities to methyl methacrylate are obtained when a phosphine having an electron-withdrawing substituent in the phenyl groups is used in combination with a strong protonic acid. Examples 26 and 27 show that high selectivities to methyl methacrylate at lower reaction rates are obtained when such phosphines are used in combination with a strong carboxylic acid and a non-carboxylic protonic acid having a pK$_a$ greater than 1.0.

I claim as my invention:

1. A process for the carbonylation of an acetylenically unsaturated compound with carbon monoxide in the presence of an alcohol and/or water, which process is carried out at a temperature in the range of from 50° C. to 200° C. in a liquid phase in the presence of a catalytic system which comprises:
   (a) a compound of divalent palladium,
   (b) an organic phosphine, and
   (c) a protonic acid, with the exception of hydrohalogenic acids, selected from a non-carboxylic acid, a carboxylic acid having a pK$_a$ not greater than 1.0 and mixtures thereof.

2. The process of claim 1 wherein said acetylenically unsaturated compound is substituted with one or more halogen atoms, cyano, ester, alkoxy, aryl or hydroxy groups.

3. The process of claim 2 wherein the organic phosphine has the general formula I

in which R¹ represents an aryl group and R² and R³ each an alkyl, cycloalkyl or aryl group, or R² and R³ together represent an alkylene or phosphacycloalkylene group.

4. The process of claim 3 wherein R¹, R² and R³ each represent a phenyl group.

5. The process of claim 3 wherein R² represents a phenyl group of R³, a chain of carbon atoms ending with the group —PR⁴R⁵, in which R⁴ represents a phenyl group and R⁵ an alkyl, cycloalkyl or phenyl group.

6. The process of claim 3, wherein the organic phosphine is a phosphine of the general formula I in which any aryl group is unsubstituted or carries an electron-donating substituent and the protonic acid is a non-carboxylic protonic acid having a $pK_a$ greater than 1.0 (measured at 18° C. in aqueous solution) or a carboxylic acid having a $pK_a$ not greater than 1.0 (measured at 18° C. in aqueous solution).

7. The process of claim 6 wherein the phosphine is triphenylphosphine.

8. The process of claim 6 wherein the phosphine is tri(p-methoxyphenyl)phosphine.

9. The process of claim 6 wherein the phosphine is 1,5-di(diphenylphosphino)pentane.

10. The process of claim 6 wherein the acid is orthophosphoric acid.

11. The process of claim 6 wherein the acid is benzene-phosphonic acid.

12. The process of claim 6 wherein the acid is pyrophosphoric acid.

13. The process of claim 6 wherein the carboxylic acid is trifluoroacetic acid.

14. The process of claim 4 wherein each of the phenyl groups carries an electron-withdrawing substituent and the protonic acid is a non-carboxylic protonic acid having a $pK_a$ not greater than 1.0 (measured at 18° C. in aqueous solution).

15. The process of claim 14 wherein the electron-withdrawing substituent is a halogen atom or a trihalomethyl group.

16. The process of claim 14 wherein the phosphine is tri(p-chlorophenyl)phosphine.

17. The process of claim 14 wherein the phosphine is tri(m-trifluoromethylphenyl)phosphine.

18. The process of claim 14 wherein the protonic acid has a non-coordinating anion.

19. The process of claim 18 wherein the protonic acid has the general formula II

wherein Z represents a sulphur or a chlorine atom and, if Z represents a chlorine atom, R represents an oxygen atom and, if Z represents a sulphur atoms, R represents an OH group or a hydrocarbon group.

20. The process of claim 19 wherein the hydrocarbon group represented by R is an alkyl, aryl, aralkyl or alkaryl group having not more than 30 carbon atoms.

21. The process of claim 20 wherein the acid is p-toluenesulphonic acid.

22. The process of claim 2 wherein the compound of divalent palladium is palladium acetate.

23. The process of claim 2 wherein in the range of from 5 to 500 mol of the organic phosphine is used per gram atom of palladium.

24. The process of claim 2 wherein in the range of from 0.5 to 50 equivalents of the organic phosphine is used per equivalent of the protonic acid.

25. The process of claim 2 wherein an ether is used as a solvent.

26. The process of claim 2 wherein said process is carried out at a total pressure range from 1 to 100 bar.

27. The process of claim 2 wherein the acetylenically unsaturated compound is an alkyne.

* * * * *